(12) United States Patent
Chen et al.

(10) Patent No.: US 7,218,390 B2
(45) Date of Patent: May 15, 2007

(54) APPARATUS AND METHODS FOR AUTOMATICALLY MEASURING A CURL OF AN OPTICAL SHEET

(75) Inventors: Jye-Jong Chen, Ping Chen (TW); Bor-Ping Wang, Ping Chen (TW); Wei-Yen Lee, Ping Chen (TW); Chih-Hao Yang, Ping Chen (TW)

(73) Assignee: Optimax Technology Corporation, Ping Chen (TW)

( * ) Notice: Subject to any disclaimer, the term of this patent is extended or adjusted under 35 U.S.C. 154(b) by 0 days.

(21) Appl. No.: 10/997,957

(22) Filed: Nov. 29, 2004

(65) Prior Publication Data

US 2006/0044553 A1    Mar. 2, 2006

(30) Foreign Application Priority Data

Sep. 1, 2004    (TW) ............................... 93126427 A

(51) Int. Cl.
*G01N 21/00*    (2006.01)

(52) U.S. Cl. .................................................. 356/237.2

(58) Field of Classification Search ...................... None
See application file for complete search history.

(56) References Cited

U.S. PATENT DOCUMENTS

| | | | | |
|---|---|---|---|---|
| 3,788,750 A | * | 1/1974 | Maltby et al. ............ | 356/239.1 |
| 4,585,343 A | * | 4/1986 | Schave et al. ............ | 356/237.2 |
| 5,019,710 A | | 5/1991 | Wennerberg et al. | |
| 5,114,230 A | * | 5/1992 | Pryor ........................ | 356/625 |
| 5,701,178 A | * | 12/1997 | Burns et al. ................ | 356/600 |

FOREIGN PATENT DOCUMENTS

JP    60-071902    4/1985

* cited by examiner

*Primary Examiner*—Michael P. Stafira
(74) *Attorney, Agent, or Firm*—Lowe Hauptman & Berner, LLC

(57) ABSTRACT

An optical sheet is moved by a conveyor belt, and at least one beam is configured above the conveyor belt. When the beam is intersected by the moving optical sheet, the optical sheet is determined to be curled. The present invention achieves automatic in-line measuring of optical sheet curls by precise optical measurement and thus enhances measuring accuracy and raises measuring speed.

16 Claims, 2 Drawing Sheets

APPARATUS AND METHODS FOR AUTOMATICALLY MEASURING A CURL OF AN OPTICAL SHEET

RELATED APPLICATIONS

The present application is based on, and claims priority from, Taiwan Application Serial Number 93126427, filed on Sep. 1, 2004, the disclosure of which is hereby incorporated by reference herein in its entirety.

BACKGROUND

1. Field of Invention

The present invention relates to a manufacturing and quality controlling method of optical sheets. More particularly, the present invention relates to an apparatus and method for automatically measuring a curl of an optical sheet in real time.

2. Description of Related Art

A liquid crystal display (LCD) has many advantages over conventional types of displays having high display quality, small volume, low driving voltage and low power consumption and being lightweight. Hence, LCDs are widely used in small portable televisions, mobile telephones, video recording units, notebook computers, desktop monitors, projector televisions and so on, and have gradually replaced the conventional cathode ray tube (CRT) as a mainstream display unit.

Polarizers are main components of a liquid crystal panel in a liquid crystal display. A polarizer can be composed of one or more optical sheets, and in addition to the polarizing function can have other functions, such as anti-peeping or optical compensation. An optical sheet may have a curl due to bad manufacturing. The curled optical sheet cannot be adhered smoothly onto the liquid crystal panel and therefore causes the liquid crystal display to have bad quality.

The prior art usually manually measures curls of optical sheets after manufacturing the optical sheets to select good optical sheets, which meet the quality control level regarding curls. However, the conventional method of manual measurement is not convenient and is also inaccurate, and thus easily causes poor quality control due to measurement errors. Moreover, manual measurement takes a long time, slows the manufacturing rate, wastes manpower and thus increases manufacturing costs.

SUMMARY

It is therefore an aspect of the present invention to provide a method for automatically measuring a curl of an optical sheet. The method measures the variation of light intensity in real time to determine whether the optical sheet is curled and is easily integrated in-line into automatic production.

It is another aspect of the present invention to provide an apparatus for automatically measuring a curl of an optical sheet, which enhances measuring accuracy, raises measuring speed, improves quality control ability and yield, saves manpower and thus reduces manufacturing cost.

In accordance with the foregoing and other aspects of the present invention, an apparatus and method for automatically measuring a curl of an optical sheet are provided. An optical sheet is moved by a conveyor belt, and at least one beam is configured above the conveyor belt. When the beam is intersected by the moving optical sheet, the optical sheet is determined to be curled.

According to one preferred embodiment of the present invention, the beam is generated by a light source and received by a detector. The light source is a laser or a lamp, and the detector is a charge-coupled device, a photomultiplier tube or a photodiode. Moreover, the apparatus further comprises a pinhole configured in the light path of the beam to enhance measuring accuracy.

According to another preferred embodiment of the present invention, a plurality of beams having different heights are configured above the conveyor belt, and the heights of the beams are sequentially decreased in the moving direction of the conveyor belt. Thus, the curled optical sheet examined by any one of the beams can be classified according to the height of the beam. A pick-up device further can be used to pick up the curled optical sheet from the conveyor belt.

In addition, the apparatus comprises a plurality of detectors arranged to receive a plurality of beams. The beams can be generated directly by a plurality of light sources, or can be formed by cooperating a plurality of beam splitters with a single light source.

The embodiments pass optical sheets under the beam between the light source (the beam splitter) and the detector by use of the conveyor belt and simultaneously measure the intensity variation of the beam. By this configuration, the embodiments achieve automatic in-line measuring of optical sheet curls by precise optical measurement, enhance measuring accuracy and raise measuring speed. Furthermore, the embodiments can be implemented automatically by photoelectric devices and a computer, and therefore are easily integrated into automatic production, which improves quality control ability and yield, saves manpower and reduces manufacturing cost.

It is to be understood that both the foregoing general description and the following detailed description are examples and are intended to provide further explanation of the invention as claimed.

BRIEF DESCRIPTION OF THE DRAWINGS

These and other features, aspects, and advantages of the present invention will become better understood with regard to the following description, appended claims, and accompanying drawings where:

DESCRIPTION OF THE PREFERRED EMBODIMENTS

Figure 1:
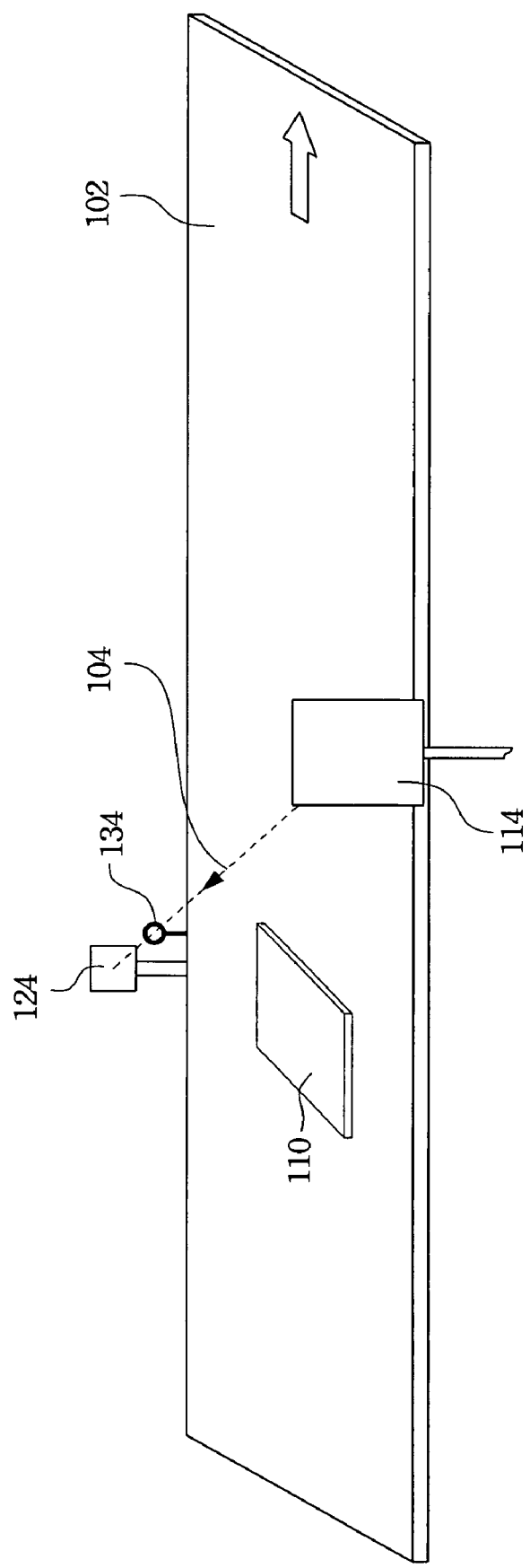
FIG. 1 is a schematic view of one preferred embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a schematic view of one preferred embodiment of the present invention. As illustrated in FIG. 1, an optical sheet 110, such as a polarizer, is moved on a conveyor belt 102. The preferred embodiment configures at least one beam 104 above the conveyor belt 102. When the beam 104 is intersected by the moving optical sheet 110, the optical sheet 110 is determined to be curled. The conveyor belt 102 is easily integrated into the conventional manufacturing process of the optical sheet, and therefore the apparatus and method of the preferred embodiment can measure whether the optical sheet 110 is curled on the production line in real time.

In the preferred embodiment, the beam 104 is generated by a light source 114 and received by a detector 124. The light source 114 can be a laser or a lamp, such as a He—Ne laser, a diode laser, a halogen lamp or other light source having suitable wavelength of which the light intensity is varied when the beam is intersected by the optical sheet 104. The detector 124 can be a charge-coupled device (CCD), a photomultiplier tube (PMT) or a photodiode. Moreover, the available wavelength of the detector 124 should comply with the wavelength of light generated by the light source 114, for better observing whether the light intensity of the beam 104 is varied due to being intersected by the curl of the optical sheet 110.

In addition, the preferred embodiment further provides several approaches to enhance measuring accuracy. For example, the preferred embodiment configures at least one pinhole 134 in a light path of the beam 104, i.e. between the light source 114 and the detector 124. The pinhole 134 is used to confine the light path to enhance measuring accuracy. Moreover, during measuring the intensity variation of the beam 104, a threshold value of the detector 124 can be adjusted to control measuring accuracy.

In short, other conventional approaches used in the prior art for enhancing measuring accuracy also comply with the scope and spirit of the present invention. Persons skilled in the prior art should easily understand and cooperate the conventional approaches with the present invention and not be limited by the foregoing approaches used in the preferred embodiment.

Figure 2:
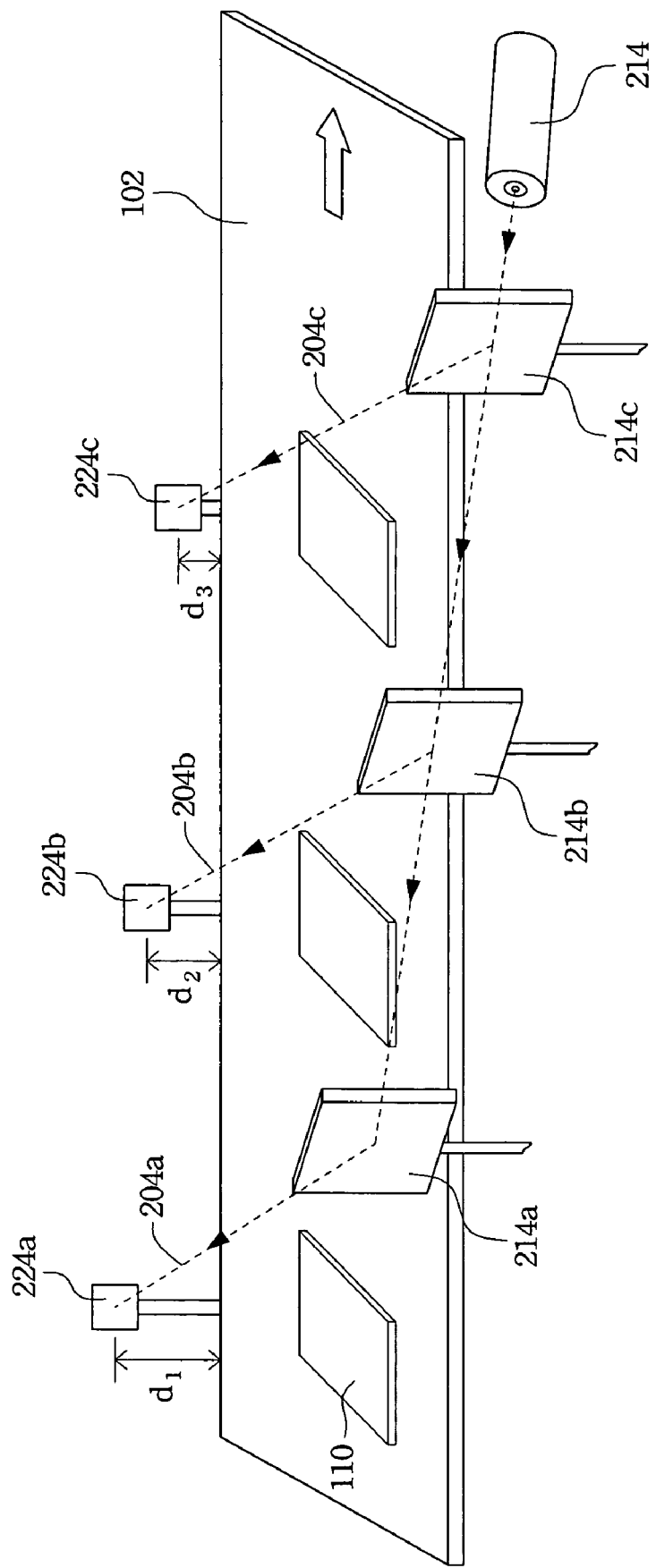
FIG. 2 is a schematic view of another preferred embodiment of the present invention.

FIG. 2 is a schematic view of another preferred embodiment of the present invention. As illustrated in FIG. 2, the preferred embodiment configures a plurality of beams 204a, 204b and 204c above the conveyor belt 102. The heights d1, d2 and d3 of the beams 204a, 204b and 204c are sequentially decreased in the moving direction of the conveyor belt 102. By this configuration, the optical sheets deemed curled by the beam 204a, 204b or 204c are classified according to the heights d1, d2 and d3 of the beams 204a, 204b and 204c. The preferred embodiment further provides a pick-up device 204, such as a mechanical arm or a vacuum chuck, to pick up the curled optical sheet from by conveyor belt 102, and classifies the sheet according to the curl level. The preferred embodiment thus achieves automatic in-line measuring and classifying of the optical sheets by their curl levels.

Moreover, the preferred embodiment uses a plurality of detectors 224a, 224b and 224c to receive the beams 204a, 204b and 204c. In another aspect, the beams with respect to the detectors 224a, 224b and 224c can be generated by a plurality of light sources (i.e. one light source to one detector); or can be formed by cooperating a plurality of beam splitters 214a, 214b and 214c with a single light source 214, as illustrated in FIG. 2. Similarly, the approaches for enhancing measuring accuracy also can be used in the preferred embodiment.

The embodiments move optical sheets under the beam between the light source (the beam splitter) and the detector by the conveyor belt and simultaneously measure the intensity variation of the beam. By this configuration, the embodiments achieve automatic in-line measuring of optical sheet curls by precise optical measurement, enhance measuring accuracy and raise measuring speed. Furthermore, the embodiments can be implemented automatically by photoelectric devices and a computer, and therefore are easily integrated into automatic production, which improves quality control ability and yield, saves manpower and reduces manufacturing cost.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for automatically measuring a curl of an optical sheet, the method comprising:
    moving an optical sheet by a conveyor belt;
    configuring a plurality of beams having different heights above the conveyor belt; and
    determining the optical sheet is curled when the beam is intersected by the optical sheet.

2. The method of claim 1, wherein the heights of the beams are sequentially decreased along with a moving direction of the conveyor belt.

3. The method of claim 1, wherein the method further comprises:
    classifying the curled optical sheet determined by one of the beams according to the height of the beam.

4. The method of claim 1, wherein the method further comprises:
    picking up the curled optical sheet from the conveyor belt.

5. The method of claim 1, wherein the beam is generated by a light source and received by a detector.

6. The method of claim 5, wherein the light source is a laser or a lamp.

7. The method of claim 5, wherein the detector is a charge-coupled device, a photomultiplier tube or a photodiode.

8. An apparatus for automatically measuring a curl of an optical sheet, the apparatus comprising:
    a conveyor belt arranged to move an optical sheet;
    at least one light source arranged to generate a plurality of beams above the conveyor belt, wherein heights of the beams are different; and
    at least one detector arranged to receive the beam, wherein when the beam is intersected by the optical sheet, the detector determines that the optical sheet is curled.

9. The apparatus of claim 8, wherein the apparatus further comprises a plurality of detectors arranged to receive the beams.

10. The apparatus of claim 9, wherein the apparatus further comprises a plurality of light sources arranged to generate the beams.

11. The apparatus of claim 9, wherein the apparatus further comprises a plurality of beam splitters arranged to cooperate with the light source for forming the beams.

12. The apparatus of claim 8, wherein the heights of the beams are sequentially decreased along with a moving direction of the conveyor belt.

13. The apparatus of claim 8, wherein the apparatus further comprises:
    a pick-up device arranged to pick up the curled optical sheet from the conveyor belt.

14. The apparatus of claim 8, wherein the light source is a laser or a lamp.

15. The apparatus of claim 8, wherein the detector is a charge-coupled device, a photomultiplier tube or a photodiode.

16. The apparatus of claim 8, wherein the apparatus further comprises:
    a pinhole configured in a light path of the beam to enhance measuring accuracy.

* * * * *